(12) United States Patent
Rumak et al.

(10) Patent No.: US 9,342,655 B2
(45) Date of Patent: *May 17, 2016

(54) GRAPHICAL DISPLAY OF ACTIONS FOR HANDLING MEDICAL ITEMS

(71) Applicant: Soft Computer Consultants, Inc., Clearwater, FL (US)

(72) Inventors: Leszek P Rumak, Dunedin, FL (US); Karen MacLennan, Palm Harbor, FL (US); Jacek A Lech, Rzezsow (PL); Andrzej Szkola, Palm Harbor, FL (US); Laura Rodrigues de Miranda, Holiday, FL (US)

(73) Assignee: Soft Computer Consultants, Inc., Clearwater, FL (US)

( * ) Notice: Subject to any disclaimer, the term of this patent is extended or adjusted under 35 U.S.C. 154(b) by 26 days.

This patent is subject to a terminal disclaimer.

(21) Appl. No.: 14/171,803

(22) Filed: Feb. 4, 2014

(65) Prior Publication Data
US 2014/0157176 A1 Jun. 5, 2014

Related U.S. Application Data

(63) Continuation of application No. 12/459,472, filed on Jul. 1, 2009, now Pat. No. 8,645,861.

(51) Int. Cl.
*G06F 3/0482* (2013.01)
*G06F 19/00* (2011.01)
*G06Q 10/10* (2012.01)
*G06F 3/0481* (2013.01)

(52) U.S. Cl.
CPC .......... *G06F 19/3406* (2013.01); *G06F 3/0482* (2013.01); *G06F 3/04817* (2013.01); *G06F 19/366* (2013.01); *G06Q 10/10* (2013.01)

(58) Field of Classification Search
None
See application file for complete search history.

(56) References Cited

U.S. PATENT DOCUMENTS

| | | | |
|---|---|---|---|
| 5,786,816 A | 7/1998 | Macrae et al. | |
| 5,841,959 A | 11/1998 | Guiremand | |
| 6,674,449 B1 | 1/2004 | Banks et al. | |
| 6,968,503 B1 | 11/2005 | Chang et al. | |
| 7,131,060 B1 | 10/2006 | Azuma | |
| 7,310,784 B1 | 12/2007 | Gottlieb et al. | |
| 8,645,861 B2 * | 2/2014 | Rumak et al. | 715/810 |
| 2003/0061266 A1 * | 3/2003 | Ouchi | 709/106 |
| 2003/0095150 A1 | 5/2003 | Trevino | |
| 2004/0196310 A1 | 10/2004 | Aamodt et al. | |

(Continued)

OTHER PUBLICATIONS

Galitz, The Essential Guide to User Interface Design, Second Edition, Wiley Computer Publishing, 2002.

*Primary Examiner* — Ryan Barrett

(57) ABSTRACT

In a system, a computer readable recording medium and a method, user input can be received in response to prompts on a display, wherein the user input may identify a processable medical item (e.g., a medical sample or medical product) and can select each of a plurality of discrete actions for handling the medical item. The actions can have an at least implied order to be performed. Based on the received user input, identification information can be stored which identifies the medical item. Action information can also be stored which represents the selected actions. Then, a flow diagram can be displayed with at least some of the action information and at least some of the identification information. The flow diagram can depict at least some of the selected actions, the actions being automatically arranged on the displayed screen in the at least implied order.

20 Claims, 12 Drawing Sheets

(56) References Cited

U.S. PATENT DOCUMENTS

| | | |
|---|---|---|
| 2005/0266494 A1 | 12/2005 | Hodge |
| 2006/0004745 A1 | 1/2006 | Kuhn et al. |
| 2006/0265249 A1 | 11/2006 | Follis |
| 2007/0016441 A1 | 1/2007 | Stroup |
| 2007/0219929 A1* | 9/2007 | Steinbach ............... 705/80 |
| 2008/0104143 A1 | 5/2008 | Khor et al. |
| 2008/0263138 A1 | 10/2008 | Heslep |
| 2009/0138284 A1 | 5/2009 | Guadagna et al. |
| 2009/0168161 A1 | 7/2009 | Guiney |
| 2009/0192823 A1 | 7/2009 | Hawkins et al. |
| 2010/0017233 A1 | 1/2010 | Toda |
| 2010/0138239 A1 | 6/2010 | Reicher et al. |
| 2010/0179852 A1 | 7/2010 | Tomizuka |
| 2011/0137702 A1 | 6/2011 | Hodges |
| 2013/0151285 A1* | 6/2013 | McLaren et al. ............ 705/3 |

\* cited by examiner

| Internal Notes | Patient Notes | Processing History | Processing Chart | Patient History | Order Entry |

Specimen Preparation

Only Currently Pending Actions

| Tube/Cont# | Samp ID | MRN | Patient Name | Spec. Type | AvailVol | Protocol | Action | Aliquot | Compl. | Next Action |
|---|---|---|---|---|---|---|---|---|---|---|
| 1198 | 09-2-A | 1432. . | D. | Plasma | 5 | XDNAX | | | ☐ | |
| 1198 | 09-2-B | | | | | | | | | |

| Order Entry 09-42 | | | | | | |
|---|---|---|---|---|---|---|
| Edit | Patient Notes | Patient History | Processing History | | | |
| HLA#: [ ] | MRN: [321...] | Nmae (L/F/M).: [Smith] [John] | | | Gender: [M] | |
| Billing #: [3315] | DOB: [ ] | Age: [ ] | Ethnicity: [ ] | | | |

| 09-42 CLLPANEL | | | | Order #: [09-42] |
|---|---|---|---|---|
| Specimen: | [PER BLD] | [Peripheral Blood] | | |
| Requested By: | [DR JONES] | [JONES, DOCTOR] | | |
| Primary Indication: | [ ] | [ ] | | |
| Test: | [CLLPANEL] | [CLL PANEL] | | |
| | | Collection D&T: [ ] | | |

| SPECIMENS | | | | | | | |
|---|---|---|---|---|---|---|---|
| Type | Description | Collected By | Collected D&T | Spec... | Status | Comment | Sent Date |
| PER BLD | Peripheral | | | | | | |

FIG.6C

| Internal Notes | Patient Notes | Processing History | Processing Chart | Patient History | Order Entry |

Specimen Preparation  ☐ Only Currently Pending Actions

| Tube/Cont# | Samp ID | MRN | Patient Name | Spec.Type | AvailVol | Protocol | Action Compl. | Next Action |
|---|---|---|---|---|---|---|---|---|
| 1198 | 09-2-A | 1432... | D. | Plasma | 5 | XDNAX | ☐ | |
| 1198 | 09-2-A | 1432... | D. | Plasma | 5 | SDNAX | | |

— 710

| Performed On | Action Name | Action D&T | Empl | Site | Worksht |
|---|---|---|---|---|---|
| Specimen A | Specimen Collected | 5/1/2009 1:06 PM | Riley | MH | |
| Specimen A | Specimen Received | 5/1/2009 1:06 PM | Riley | MHL | |
| Tube Protocol XDNAX | Tube Received | 5/1/2009 1:06 PM | Riley | MHL | |
| Order | Order Inserted | 5/1/2009 1:06 PM | Riley | MHL | |
| Test EBV | Added Test | 5/1/2009 1:06 PM | Riley | RDL | |
| Text CMVP | Added Test | 5/1/2009 1:06 PM | Riley | MHL | |
| Test HSV | Added Test | 5/1/2009 1:06 PM | Riley | MHL | |

712 —

Planned Aliquot Tubes

| Tube#: | Tube ID: | Tube Type: | Vol. | Protocol | Att Tests | Sample ID: |
|---|---|---|---|---|---|---|
| 1198 | 09-2-A | LT6 | | XDNAX | HSV | G09-250-A02-00 |
| 1199 | 09-2-B | LT6 | | SDNAX | EBV | G09-250-A03-00 |

GRAPHICAL DISPLAY OF ACTIONS FOR HANDLING MEDICAL ITEMS

CROSS-REFERENCE TO RELATED APPLICATION

This application is a continuation of U.S. application Ser. No. 12/459,472 filed Jul. 1, 2009, now U.S. Pat. No. 8,645,861, the disclosure of which is incorporated herein by reference.

BACKGROUND

1. Field of the Invention

The subject matter of the present application relates to a medical information processing system, and more specifically, to a system, recording medium and a method for graphically displaying actions in handling a medical item such as a medical specimen or a medical product.

2. Description of Related Art

Medical information processing systems are commonly used to track the processing of medical items such as medical specimens and medical products in medical testing laboratories. Heretofore, the ways in which information concerning the processing of a medical item is displayed on a screen of a workstation or other computing devices have not been optimum. When actions for handling a medical item are displayed only in form of text, users may have some difficulty recognizing the sequential order in which tests are to be performed and in what stage of testing a medical sample is at the current time. For example, it may not be readily apparent from a screen summarizing actions to be performed that some actions need to be performed sequentially, i.e., one action at a time before proceeding to the next action, and that other actions should be performed in parallel, that is, at the same time, such as on separate portions of a medical specimen.

SUMMARY

In accordance with an aspect of the invention, an improvement can be provided by graphically displaying the actions for handling a medical item. In such way of representation, actions to be performed in parallel can be easily distinguished by the users from actions to be performed sequentially. With such graphical display, the user can easily recognize when some actions should be performed prior to performing other actions and when not yet performed actions must be performed only after certain other actions have been performed. Thus, a graphical display can help users to recognize more easily the sequence in which actions in a test order should be performed.

In one embodiment, a graphical display screen can be displayed automatically by the medical information processing system when the user operates a "Processing Chart" tab that appears on a screen. The Processing Chart screen can be displayed in form of a flow diagram which displays actions in an order they are to be performed, together with arrows indicating which action is to be performed next. The flow diagram can be displayed automatically, without requiring additional input from the user beyond the input information provided by the user in inputting or processing an order for tests in accordance with prompts displayed on a screen. As displayed graphically on the screen, the actions in an order for tests can be shown beginning with an action of "Order Entry" near one edge of the screen. Subsequent actions can appear on the screen to the right of the Order Entry action, and the flow between actions can be shown by arrows, for example, such that the actions in the order proceed generally in a direction towards another edge of the screen. For example, the sequence of actions can be displayed in a left-to-right direction across the screen. In one example, actions performed in parallel can be depicted by multiple arrows pointing away from one action to a plurality of separate actions. The arrows and subsequent actions to be performed in parallel can be displayed, for example, in parallel rows of actions on the screen. Some or all of the actions specified by a particular order for tests can be displayed on the same screen. For an order for tests that involves a relatively large number of actions, the actions can be displayed in a form larger than can be displayed on a single screen at one time, and the user can scroll the screen to view a portion of the screen that is not currently displayed.

Each action can be displayed with an icon representative of the type of action to be performed. For example, an action "Order Entry" can be displayed with an icon that is representative of a screen when an order of tests is entered in the system. An action that involves a medical specimen, for example, "Tube Received" can be displayed with an icon representative of liquid in a test tube. The display of some or all actions can be accompanied with text description that identifies the sample or product used in that action.

An information processing system can be provided in accordance with an aspect of the invention which includes a processor and instructions executable by the processor to perform a method. Such method can be performed, for example, by receiving user input in response to prompts on a display, wherein the user input identifies a processable medical item (e.g., a medical sample or medical product). The user input can select each of a plurality of discrete actions for handling the medical item. The actions can have an at least implied order to be performed. Based on input received from the user, information that identifies the medical item can be stored. Action information can also be stored which represents the selected actions. Then, a flow diagram can be displayed with at least some of the action information and at least some of the identification information. The flow diagram can depict some or all of the selected actions, the actions being automatically arranged on the displayed screen in the at least implied order.

In accordance with another aspect of the invention, a computer-readable recording medium is provided in which a plurality of instructions has been recorded thereon, and in which the instructions are executable by a processor to perform a method having steps as are described above.

In accordance with another aspect of the invention, a method is provided, which has steps as are described above.

BRIEF DESCRIPTION OF THE DRAWINGS

FIG. 5 schematically illustrates a screen for a specimen preparation function which can be displayed in accordance with an embodiment of the invention.

FIG. 6B schematically illustrates an order entry browser screen, from which an order entry function can be accessed in accordance with an embodiment of the invention.

FIG. 6C schematically illustrates an order entry screen having prompts for receiving user input for creating an order for one or more tests in accordance with an embodiment of the invention.

FIG. 7 schematically illustrates a screen which can display a table of actions in accordance with an embodiment of the invention.

DETAILED DESCRIPTION

Figure 1:
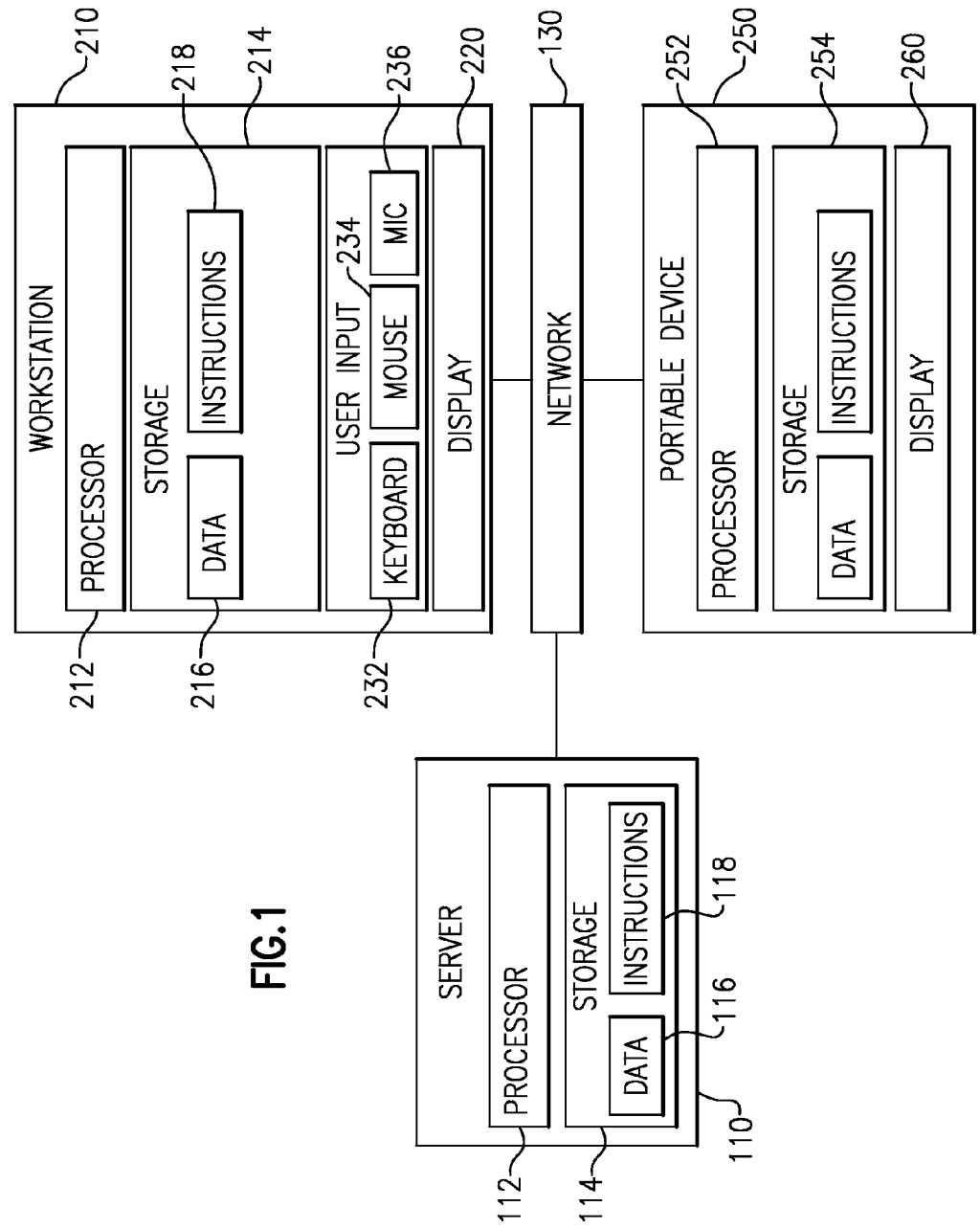
FIG. 1 is a schematic diagram illustrating a medical information processing system in accordance with an embodiment of the invention.
Figure 2:
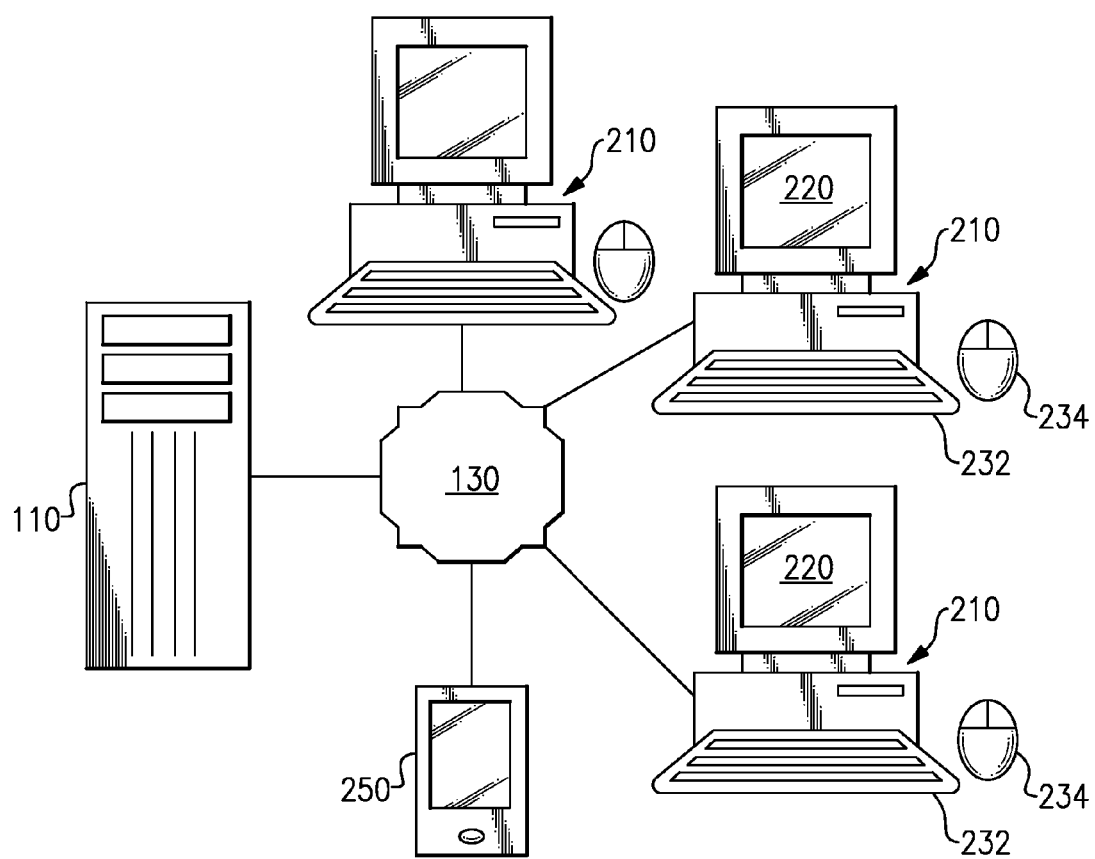
FIG. 2 is a schematic diagram further illustrating a medical information processing system in accordance with an embodiment of the invention.

As shown in FIGS. 1 and 2, a medical information processing system in accordance with an embodiment of the invention includes a computer 110, for example, a server having a processor 112 that may include one or more microprocessors. Storage 114 is available for storing and retrieving information used by the processor. For example, storage 114 may be used to store data 116 and instructions 118 which are executable by the processor. Storage can include, for example, one or more of various magnetic, solid-state or optical drives, etc., for read-write access to data and instructions. The storage can also include one or more various portable memory media which can be read-write type, read-only type or combination type (e.g., a type of medium designed to be written only once but read many times), which can be recorded or read by electrical, magnetic, or optical means. For example, the storage can include an external memory drive or miniature memory card, e.g., SD card or drive, a compact disc ("CD") or CD-ROM, digital versatile disc ("DVD"), magnetic tape media, etc., which are easily and readily interchangeable with other similar media, and on which data or instructions or both can be recorded, read and, in some cases, executed by computer 110.

The instructions 118 can be any instructions which are executable by the processor, such as machine language instructions, or can be in any computer language such as source code which is compiled in advance of execution or interpretable code which is interpreted during execution. The data can be handled, i.e., written to storage or retrieved therefrom or modified based on the execution of the instructions 118 by the processor. Although the storage 114 is shown together with processor 114 in computer 110, the storage may or may not be housed together with the processor in the same physical unit.

In one example, a network 130 can be used to facilitate communication between the computer 110 as one node of the network and one or more workstations 210 which can operate as one or more additional nodes. The three workstations 210 shown in FIG. 2 are merely illustrative, as there can be fewer or more workstations capable of connecting to a server 110 or to each other through a network 130. The network 130 can include one or more types of networks, such as, but not limited to: an enterprise network for the primary use or control by a particular organization, an intranet, i.e., a non-public network operating in accordance with the communication protocol known as Internet Protocol, or can be another type of a private or virtual private network, etc. The network 130 can include portions extending within a public network such as the Internet. In such case, provisions can be made for secure connections through the Internet to satisfy security and quality-of-service goals. Communications between nodes can be facilitated by any of a variety of network communication protocols, such as, without limitation, wired or wireless communication protocols.

Like computer 110, workstations 210 typically include a processor 212 (FIG. 1) and are capable of storing and retrieving data 216 and instructions 218 from associated storage 214 which may be housed together with the processor or separately therefrom. The workstation typically includes a display 220, e.g., a screen capable of electronically displaying still or moving images or both, which is capable of displaying information to a user in a form readable or recognizable by the user. Devices such as a keyboard 232 and a mouse 234, trackball or other pointing device typically are provided for registering user input. The display, keyboard, mouse (or both) can together facilitate inputting of user information through a graphical user interface ("GUI") such as a Windows® operating system-enabled display (Windows is a registered trademark of Microsoft Corporation). For example, user input may be of a type which causes the display of information presented to the user at a particular location on the screen to be modified when the user selects the location using a mouse or other pointing device.

A portable computing device 250, e.g., typically a handheld computer such as a personal digital assistant, e.g. Blackberry type device, or cellular phone type device, which may have a wireless interface or a wired (contact-based) interface may also be provided which can connect with computer 110 or a workstation 210 through network 130. Like computer 110, the portable device 250 can have a display 260 for presenting information to the user and typically has one or more of a keyboard (not shown) or keypad (not shown) and pointing device (not shown) for registering user input therewith. Like computer 110, portable device 250 has a processor 252 and storage 254 for the storage of instructions for execution by processor 252 to retrieve, store or modify data. Although some functions may be indicated below as being performed on a server and other functions may be indicated as being performed on a workstation, various aspects of a system and method may be implemented by a single computer.

A specific example of a medical information processing system facilitating graphical display of actions for handling a medical item will now be explained with reference to the following description and accompanying figures. A medical specimen can be an item such as a tissue specimen or sample of a bodily fluid, for example, which is collected for testing, among other uses. For example, samples of blood and urine are specimens commonly collected from patients for testing. A sample of tissue removed from a suspected cancerous part of the body can also be a medical specimen, and a sample of tissue removed from a part of the body believed to be healthy can also be a medical specimen. As will be described further below, actions performed during processing of the specimen can be planned, modified and tracked by user interaction with a screen using a graphical display facility in accordance with an embodiment herein.

In a broad application of the principles described herein, a medical specimen can be an item collected from a deceased person, animal, plant or other living thing or formerly living thing. A medical product, by comparison, typically is something which is prepared, directly or indirectly, from a medical specimen. For example, a partial or complete DNA (deoxyribonucleic acid) sequence is a product which can be prepared from an appropriate sample, such as a blood sample.

A facility for graphically displaying actions relating to handling of medical items can be included in a program containing a set of instructions executable by a computer to facilitate operation of a medical information processing system. Typically, such graphical display facility can be used together with a suite of programs for the diagnosis or treatment of medical conditions. Alternatively, such graphical display facility can be provided as a stand-alone program for execution independently from another program.

Figure 3:
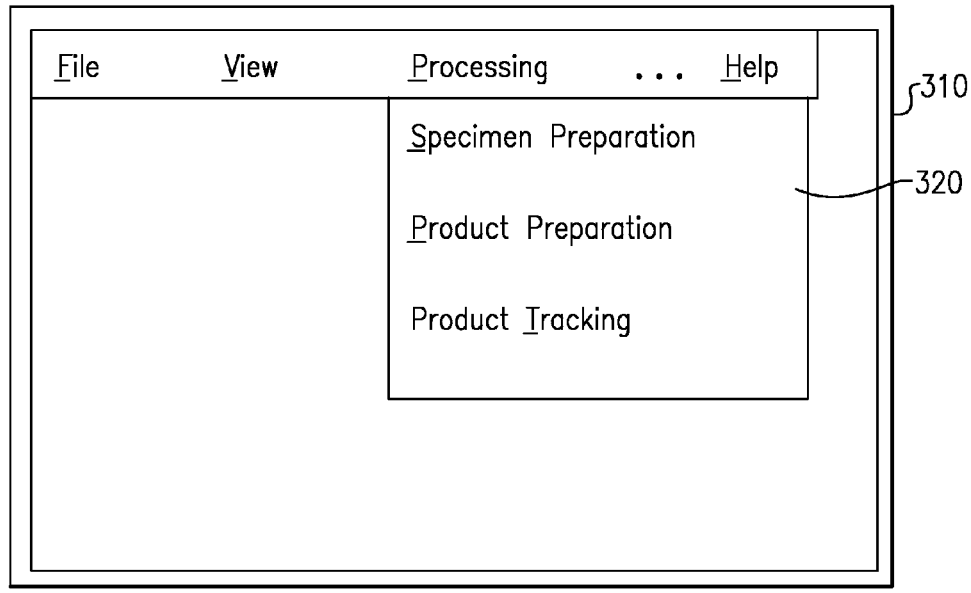
FIG. 3 schematically illustrates a screen which can be displayed in accordance with an embodiment of the invention.

Typically, in such suite of programs, a user at a workstation 210 is prompted by information displayed on a screen at a workstation to provide certain information for handling of the medical item. This step typically occurs after the user logs on to the medical information processing system, i.e., authenticates, by successfully entering user identification (a "USERID") and a password and possibly other required information. This step typically is performed via user input provided at a keyboard or pointing device or both in response to one or more prompts presented on the workstation's display. As seen in FIG. 3, a particular processing procedure for handling medical item (specimen or product) may be selected from a pull-down menu 320 appearing on the screen 310 during execution of a program. For example, the pull-down menu in FIG. 3 displays some options available for preparation of a specimen ("Specimen Preparation"), preparation of a product ("Product Preparation", or the tracking of a product ("Product Tracking"). The menu can display fewer or more items as desired.

Figure 4:
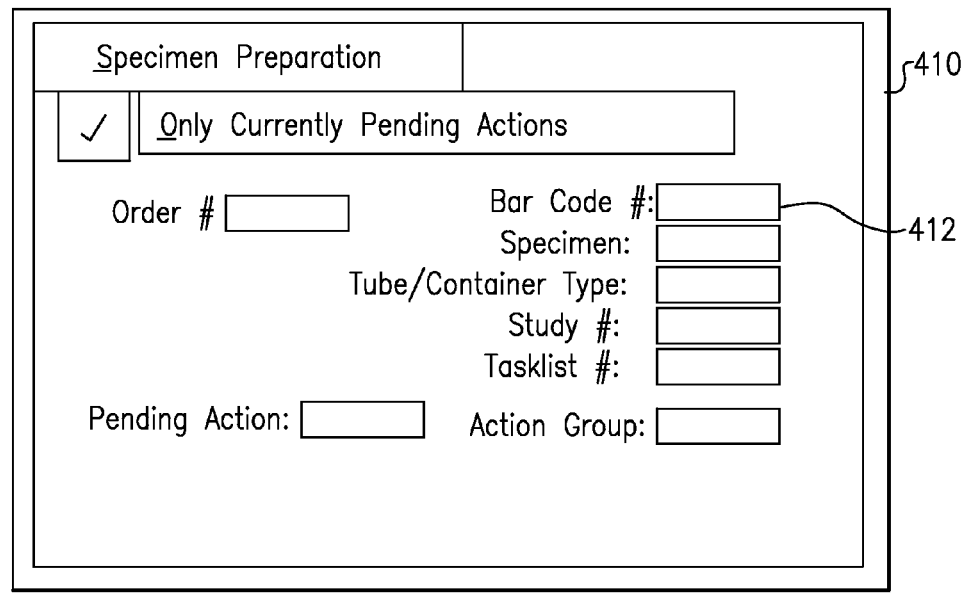
FIG. 4 schematically illustrates a screen for a specimen preparation browser function which can be displayed in accordance with an embodiment of the invention.

When the user chooses "Specimen Preparation", a Specimen Preparation browser window 410 may now appear (FIG. 4) on the display screen. As seen therein, the browser window 410 can be displayed as a form having several input boxes 412 for receiving user input. The input boxes on the browser window can be used to search for and retrieve one or more stored records of medical samples which relate to a particular medical specimen in some way. By checking the box on the screen next to "Only Currently Pending Actions" the user can use the browser window to retrieve only records that relate to currently pending actions, i.e., which relate to actions concerning the testing of a medical specimen or product which has not yet been completely performed. Each action typically refers to some discrete item of work to be performed in handling the specimen. The action can be one of several types of actions which are pre-defined before the user inputs an order using the current specimen. For example, collecting a specimen, e.g., a blood sample, from a patient is one action. Another action can be an "aliquot" which means dividing the specimen by placing a portion of the specimen into a separate test tube. After the aliquot, the resulting portions of the specimen can then be processed in parallel in accordance with different actions. Other actions, as described below, relate to particular tests performed on a sample. Using the specimen preparation browser window 410, the user can view a screen (not shown) that contains only actions that relate to testing still to be performed at one stage or another.

In addition, the user can input information such as a number identifying the "Specimen:" and retrieve records from storage which bear the same specimen number. Alternatively, the user could input a "Bar Code#:", a number which matches an optically readable bar code which can appear on a label affixed to a specimen. For example, a Bar Code# can appear with the bar code on as label adhesively attached to a tube containing a blood sample. Then, the browser window would retrieve records which contain the same bar code number, and thus, would match the specimen. In such way, by inputting a Specimen or a Bar Code#, the user can retrieve records relating to a particular sample, in order to update such records or add or modify actions to be performed with respect to the sample, as will be described below.

Another way records can be retrieved is by the user inputting a number in the box labeled "Order#" to identify the order for medical testing to which the specimen belongs. After retrieving the matching records, an existing order can be modified or augmented by inputting information specifying additional actions to be performed, as described below.

In one example, the user can also input information identifying the Action Group. The Action Group can indicate what stage of testing the action belongs to. For example, an Action Group "A" can relate to collecting a specimen and performing some initial step such as verifying receipt of a tube that contains the specimen at a laboratory. Another Action Group, for example, Action Group "B" can relate to performing tests on the sample. Yet another Action Group "C" can relate to reviewing and signing off on results of tests that have been performed.

FIG. 5 shows a specimen preparation screen that can be displayed when the user selects currently pending actions based on a particular criterion, for example, specimens which match a particular Order#. Information concerning the matching specimens then can be displayed in form of the table 510 shown in FIG. 5. For example, as shown in FIG. 5, the displayed table contains information identifying a tube or container number ("Tube/Cont#) and information identifying the particular specimen as "Samp ID". In addition, the displayed table can also include other information such as medical record number ("MRN") and the patient's name. The table can further identify the type of sample, which can be "Plasma" for example, as listed in FIG. 5. When the specimen is in liquid form, the table can indicate the volume of the sample as "AvailVol". In this case, the table indicates the available volume in milliliters and indicates the sample has 5 milliliters available volume.

Each row of the table 510 typically relates to a discrete action to be performed relative to the sample. For example, the action to be performed in accordance with the uppermost displayed row of the table 510 is indicated under the column header of "Action" as "aliquot". The table may further contain a check box to be marked when the action has been completed. The column marked "Next Action" can indicate the next action to be performed on the sample which is listed in the same row of the table, as will be described in further detail below.

A particular protocol for testing the specimen can be indicated in the column labeled "Protocol". In this case, the displayed table 510 lists one protocol "XDNAX" for testing the specimen. A protocol refers to a predefined sequence of actions to be performed with respect to a sample, such as when attempting to determine whether the sample does or does not show evidence of a particular medial condition in a patient. For example, the protocol may identify a sequence of actions to be performed to test the sample for Epstein-Barr virus. The protocol typically is formulated in advance of inputting the current action and the current order. The protocol typically is formulated by a medical doctor such as a pathologist or other medical professional to specify a sequence of actions to be performed when an order is inputted to the medical information processing system to test a particular condition for a patient, for example, Epstein-Barr virus.

The screen displayed in FIG. 5 can also contain several toolbar buttons including "Internal Notes", "Patient Notes", "Processing History", "Processing Chart", "Patient History" and "Order Entry", among others, which can be selected by user input (e.g., by a pointing device such as a mouse) to display other screens or menus which provide certain functions to the user.

Figure 6A:
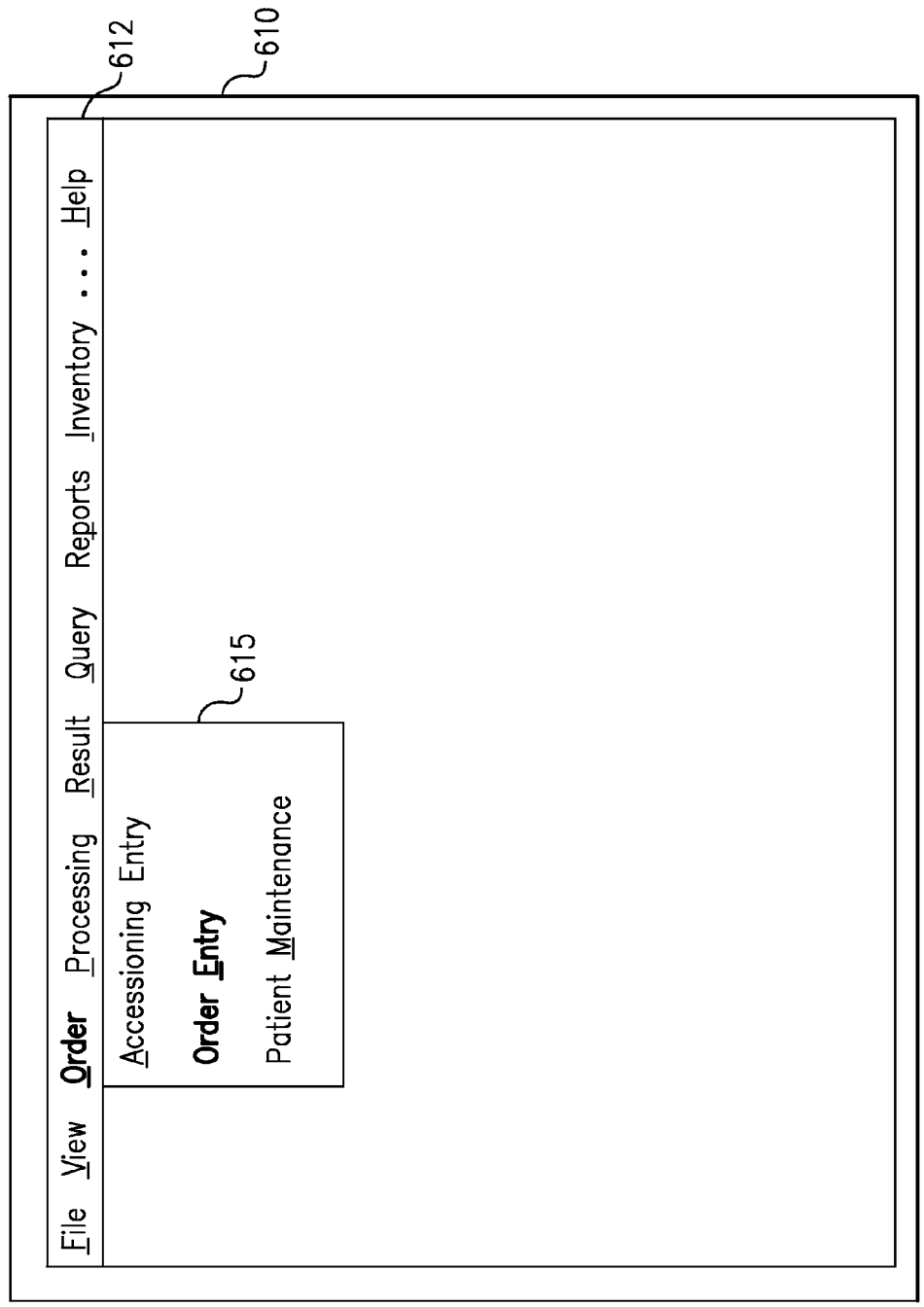
FIG. 6A schematically illustrates a main menu screen having a toolbar menu, from which an order entry browser screen can be accessed in accordance with an embodiment of the invention.

FIG. 6A illustrates a main menu screen 610 of a medical information processing system according to the present invention. The screen 610 contains a menu toolbar 612 toolbar buttons "File", "View", "Order", "Processing", "Result", "Query", "Reports", "Inventory", "Help", among others. Using a pointing device such as a mouse, the user can select the "Order" button, and a pulldown menu 615 appears which contains several options, including "Order Entry". Other options such as "Accessioning Entry" and "Patient Maintenance", among others, may appear on the same pulldown menu.

Figure 6B:
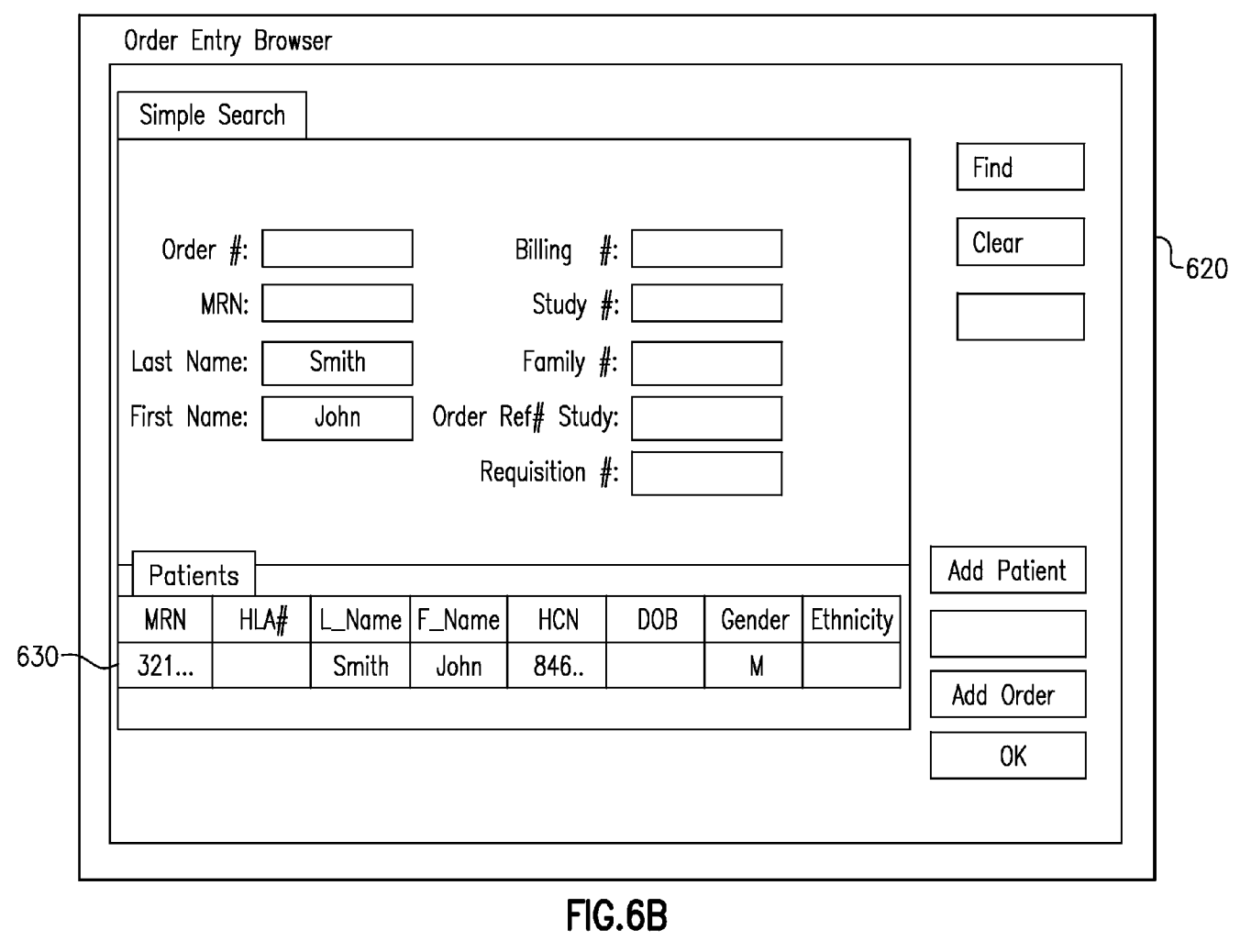

When the user selects "Order Entry" from the pulldown menu 615, an order entry browser screen 620 such as illustrated in FIG. 6B can appear. This screen 620 includes a search function, e.g., as illustrated, "Simple Search" through which the user can retrieve existing orders by entering information in the input boxes adjacent to the prompts for an order number ("Order #"), MRN, the patient's "Last Name", "First Name", and other criteria which appear in FIG. 6B, such as "Billing #", "Study #", "Family #", "Order Ref# Study" and "Requisition #" etc. After entering information in one or more such input boxes, the user can then operate the "Find" button on the screen. This will then retrieve information, if any, that matches the inputted information.

To proceed in inputting an order for test(s), a patient record must exist for the patient for whom the test(s) will be ordered. The order entry browser screen permits the user to quickly determine whether the patient record already exists or whether a new patient record needs to be created. In an example of operation, when the user enters a patient's Last Name "Smith" and First Name "John" in the corresponding input boxes and then operates the "Find" button, the screen 620 can then display a table containing information concerning the patient together with additional information about the patient's identity such as the values of MRN, HLA#, HCN, DOB, Gender and Ethnicity stored in a record for the patient in a database. From the displayed patient information, the user can confirm whether it relates to the same patient for which the user needs to input the order. After confirming the displayed information matches the actual patient, the user can then operate the "Add Order" button on the screen to navigate to a different screen 650 (FIG. 6C) and then input the order.

On the other hand, when the user searches for a patient record using the Order Entry Browser screen 620 but the system does not retrieve patient information which matches such patient, the user then needs to create a patient record. The screen 620 provides an "Add Patient" button which permits navigation to another screen (not shown) where a patient record can be created for the patient for whom the test(s) is ordered.

FIG. 6C illustrates an "Order Entry" screen that is displayed after the user operates the "Add Order" button after confirming that a matching patient record exists. As seen in FIG. 6C, the screen may be divided into different areas 660, 670, 680 for displaying different types of information. For example, an upper screen area 660 can display patient information such as name, MRN, age, etc., which are retrieved from a patient record stored in the medical information processing system. A middle screen area 670 can display prompts and corresponding input boxes for inputting an order for tests. A lower screen area 680 can display other information. For example, the lower screen area 680 can be captioned "SPECIMENS" and can display information relating to one or more specimens to be collected for performing a test which is the subject of the order being inputted by the user. The specimen information can be displayed in tabular form with headings for information identifying "Type", "Description", "Collected By", "Collected D&T" (collected date and time), "Spec . . . ", "Status", "Comment", "Sent Date", etc. The screen may also display a heading "Order Entry 09-42" which identifies the particular screen as well as the order number "09-42" for the current order that the user is entering on the screen.

A toolbar 654 has buttons "Edit", "Patient Notes", "Patient History", "Processing History", etc, which when selected, such as by the user, allow access to various functions. When the "Edit" button is selected, the user can input an order for tests. In FIG. 6C, the user can be prompted to identify a type of specimen to be collected in the input box adjacent to "Specimen" in the middle area 670 of the screen. The user may then select a type of "PER BLD" (Peripheral Blood). The user may be prompted to select or input a particular test or test protocol in the box adjacent to "Test:", which in this case, the user has selected "CLL Panel". Typically, the user is also required to select or input the name of the medical professional ordering the test, for example, "DOCTOR JONES", to appear in the input boxes adjacent to "Requested By:". The user is also prompted to identify the "Primary Indication" for performing the test. The "Primary Indication" can prompt for a primary diagnosis of the patient, which could be, for example, "leukemia".

FIG. 7 illustrates a table 710 that can be displayed when the user operates the "Processing History" tab provided on a screen, for example, the tab provided on the Specimen Preparation screen (FIG. 5) or on the Order Entry screen (FIG. 6). As seen in FIG. 7, the table 710 can be displayed in a pop-up window which overlays a portion of the screen 510 (FIG. 5). Alternatively, the table 710 can be incorporated in the same window in which the other content of FIG. 7 including the buttons "Internal Notes", "Patient Notes", "Processing History", "Patient History" and "Order Entry", among others, are displayed.

The information in the table 710 can be organized by the sequence of actions to be performed with respect to a sample. As seen in FIG. 7, the actions are shown in sequence from the uppermost displayed row 712 to one or more rows which follow such action to a lower displayed row 722. The user may have the ability to scroll upwards in a row-wise direction of the table from row 722 towards row 712 and may have the ability to scroll downward in a row-wise direction of the table from row 712 towards row 722. Actions of type "aliquot" 724, i.e., actions which call for splitting a sample into two or more divided samples, can be set off in a different section of the table from other actions to be performed or can be displayed in a different table. In one embodiment, the sequence in which the actions are displayed in the table 710 is determined by a protocol assigned to the test order. The row order in which actions are displayed can match the order in which actions are performed in accordance with such protocol. However, in the example of FIG. 7, some of the actions, for example, an EBV test (Epstein-Barr virus), CMVP test (cytomegalovirus plasma) and an HSV test (herpes simplex virus), although represented on succeeding rows of the table 710, are intended to be performed in parallel, instead of in sequence.

An improvement can be made in the way actions are displayed in FIG. 7 so that actions that should be performed in parallel can be distinguished easily by the user from actions that should be performed in sequence. An improvement can be made in displaying actions that are performed prior to performing other actions. Moreover, an improvement can be made in displaying not yet performed actions that must be performed only after certain other actions have been performed. In that way, the user may recognize more easily the sequence in which actions in the test order should be performed.

Figure 8:
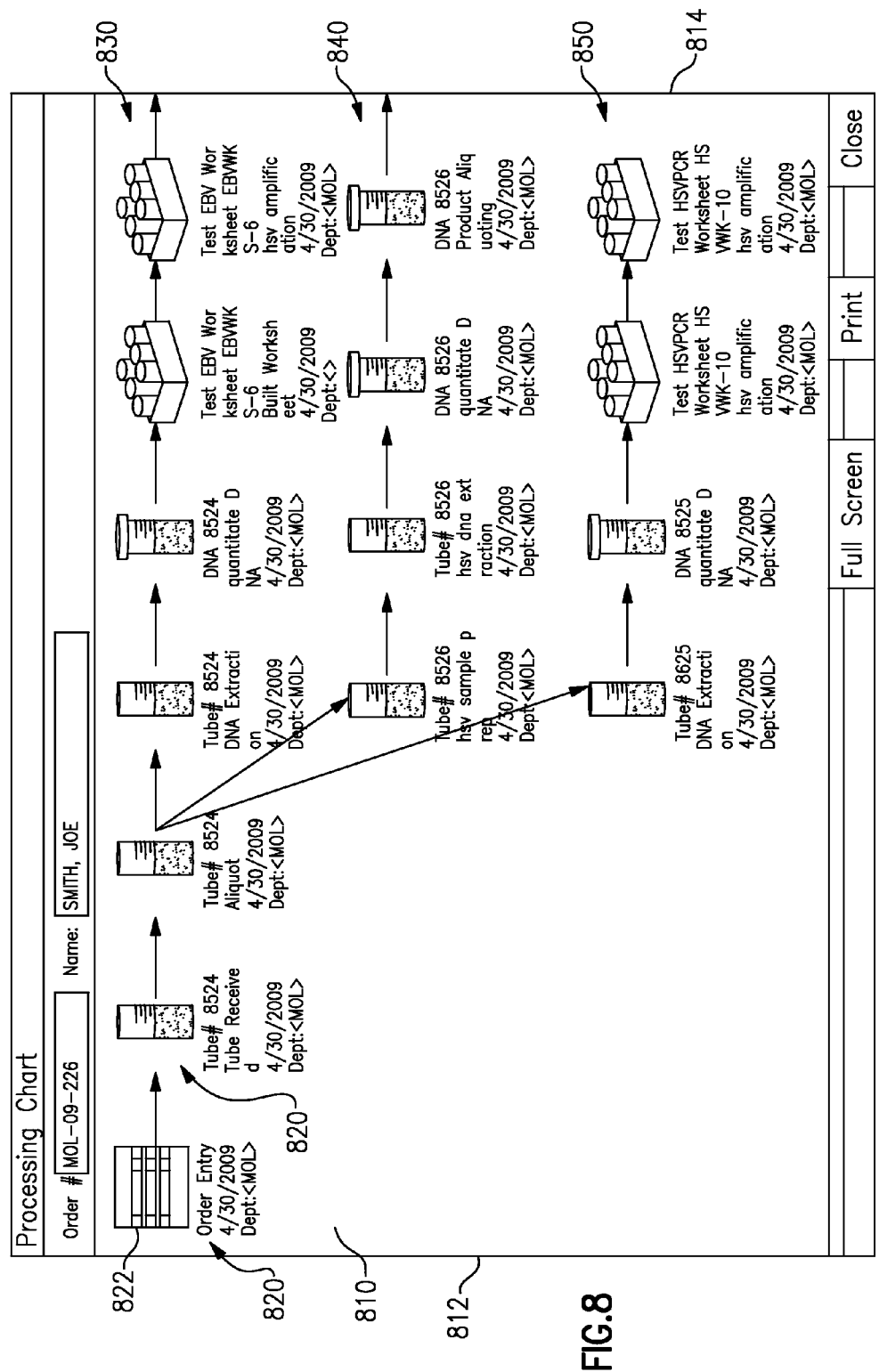
FIG. 8 schematically illustrates a screen containing a flow diagram which can be displayed in accordance with an embodiment of the invention.

FIG. 8 shows a screen which can be displayed automatically by the medical information processing system when the user operates the "Processing Chart" tab that appears on a screen such as one of the screens of FIG. 5, 6 or 7. As seen in FIG. 8, the Processing Chart screen is a flow diagram which displays actions 820 in an order they have been performed, together with arrows indicating which action is to be performed next. The flow diagram is displayed automatically by the medical information processing system, i.e., without requiring additional input from the user beyond that already provided in inputting a test order, as described above. The screen also contains buttons which allow the user to view the display in "Full Screen" mode, or to print or close the screen.

Figure 9:
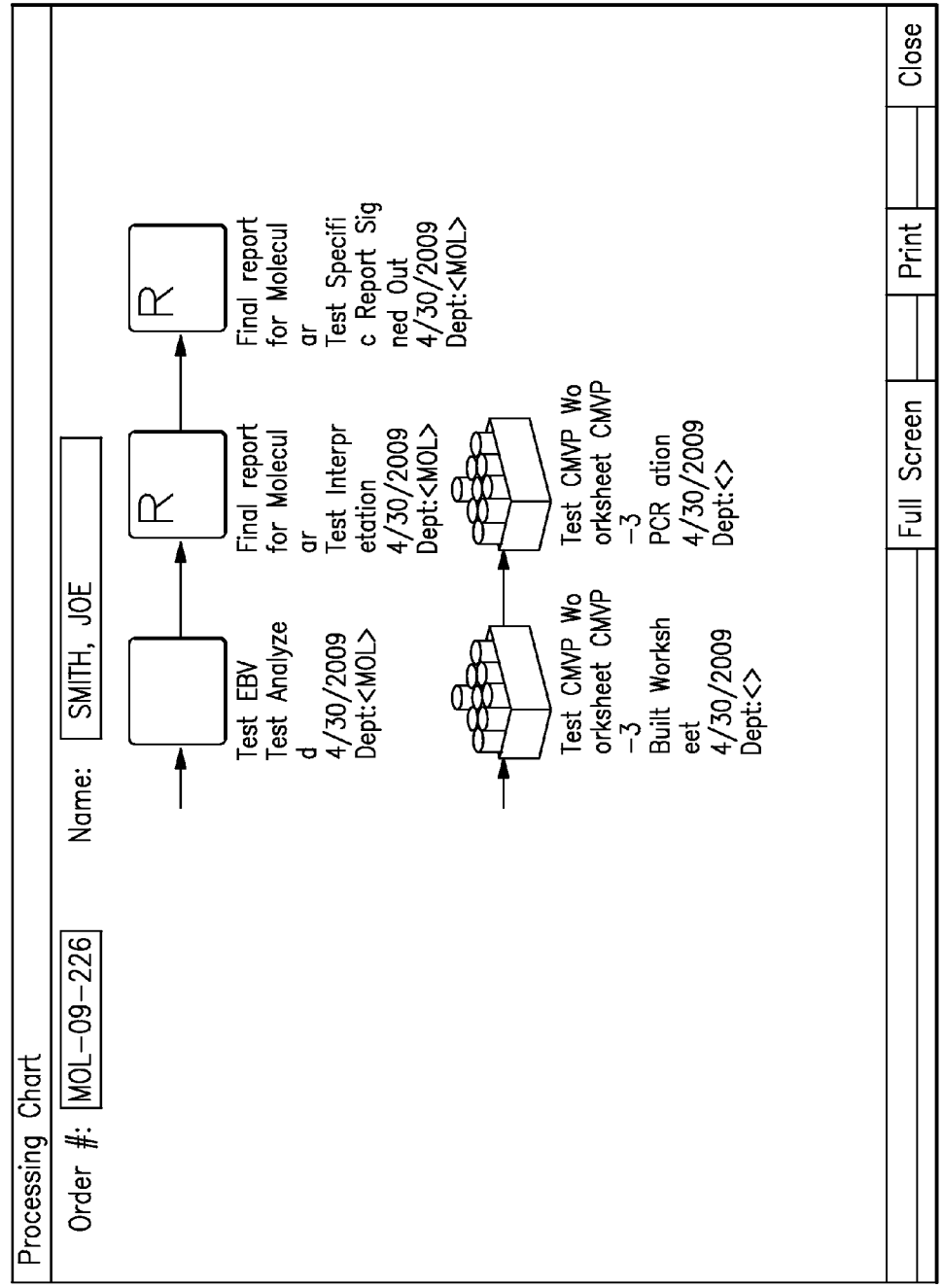
FIG. 9 schematically illustrates another screen containing a continuation of the flow diagram shown in FIG. 8 which can be displayed in accordance with an embodiment of the invention.

As seen in FIG. 8, the actions are displayed beginning with an action of "Order Entry" near the left edge 812 of the screen and continue in the order each action is performed in a direction towards the right edge 814 of the screen. Some or all of the actions specified by a particular order for tests can be displayed on the same screen. For an order for tests that includes a relatively large number of actions, the actions can be displayed in a form larger than can be displayed on a single screen at one time. Thus, FIG. 8 only shows a part of the actions to be performed in the order. FIG. 9 shows a result of scrolling to the right to display additional actions that could not be displayed at the same time as the actions shown in FIG. 8. The actions in FIG. 9 are actions which follow the actions shown in FIG. 8. Here, in this case, the action "Test EBV Test Analyzed" in FIG. 9 is performed following the action "Test EBV Worksheet EBVWKS-6 HSV amplification" (FIG. 8). Similarly, the action "Test CMVP Worksheet CMVP-3 Built Worksheet" in FIG. 9 is performed following the action "Test HSVPCR Worksheet HSVWK-10 HSV amplification" (FIG. 8).

Of course, there is no requirement that an action which occurs later than another action in the sequence always be displayed to the right of the earlier action. A later action could be displayed to the left of an earlier action or above or below the earlier action, and the direction of flow could be indicated in each case by an arrow. Some users may prefer that a later action be displayed to the left of an earlier action or above or below an earlier action. In a particular country, it may be conventional to order items from right-to-left, up-to-down, down-to-up, or other arrangement. The medical information processing system may provide an option for the user to input a preference concerning the flow direction, i.e., the direction that arrows typically run between earlier actions and later actions. The medical information processing system may designate by default the direction in which the flow between actions is displayed, and may designate the default direction differently depending upon the country in which the medical information system is used.

Each action can be displayed with an icon representative of the type of action to be performed. For example, as seen in FIG. 8, the "Order Entry" action is displayed with an icon 822 that is representative of a screen displayed when entering an order for testing. An action that involves a medical specimen, for example, "Tube Received" is displayed with an icon representative of liquid in a test tube. The arrows in FIG. 8 graphically illustrate information about the order that actions are performed. FIG. 8 shows that the action "Tube Received" is performed immediately after the action "Order Entry", and also shows that the action "Aliquot" is performed immediately after the action "Tube Received".

As further seen in FIG. 8, three separate arrows point away from the action "Aliquot" to three separate actions involving three divided samples resulting from the division of the original sample by the aliquot. The arrows and subsequent actions to be performed in the actions displayed in each of a top row 830, middle row 840 and lower row 850 of the screen indicate that handling of the sample is now to proceed in parallel with respect to each of the divided samples obtained by the aliquot. Accordingly, FIG. 8 shows that the actions in the top row 830 of screen 810 are to be performed in parallel with the actions in the middle row 840 of the screen. In addition, FIG. 8 shows that the actions in the lower row 850 of the screen are to be performed in parallel with the actions in the top and middle rows 830, 840 of the screen.

As further seen in FIG. 8, the display of some or all actions can be accompanied with text identifying the sample or product used in that action. For example, the arrows pointing away from "Aliquot" point to actions that involve different aliquot samples identified as Tube#8524, Tube#8525 and Tube#8526. Moreover, as displayed in the top row 830 of FIG. 8, three actions are Specimen actions identifying Tube#8524 and one action is a Product action quantifying a DNA product 8524 obtained from Tube#8524. In addition, in the middle row 840 of FIG. 8, two actions are Specimen actions which identify Tube#8526 and one action is a Product action that processes a DNA product 8526. Similarly, in the bottom row 850, one action is a Specimen action identifying Tube#8525 and one action is a Product action quantifying a DNA product 8525 obtained from Tube#8525. The displayed text can help the user to positively identify each sample or product to be handled in each action.

Figure 10:
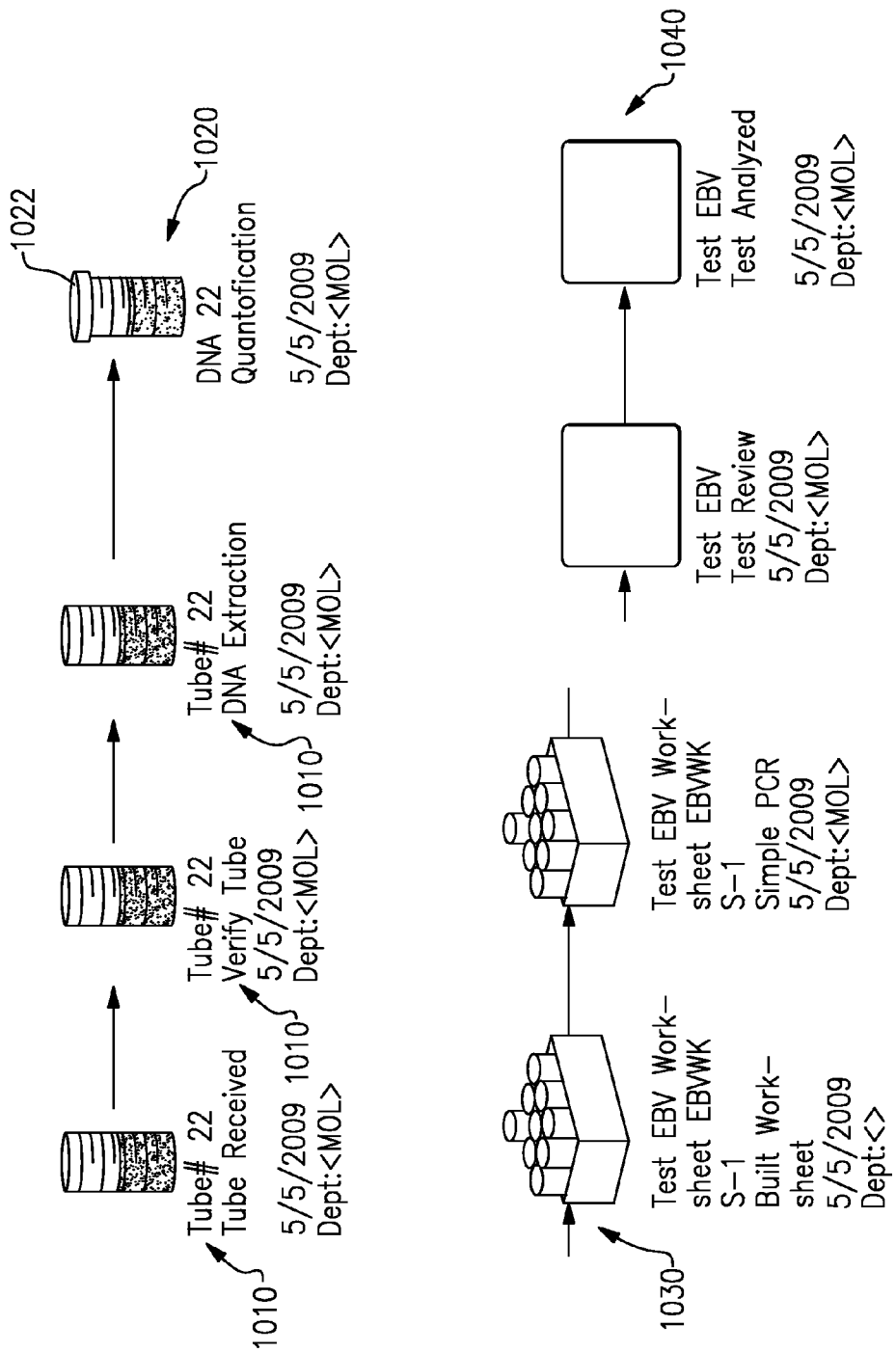
FIG. 10 illustrates different types of icons which can be displayed on a screen containing a flow diagram in accordance with an embodiment of the invention.

FIG. 10 illustrates differences in the display of icons and text for four different types of actions. As noted above, actions 1010 that relate to specimen handling can use an icon that graphically represents a test tube and may identify the specimen by Tube#. On the other hand, an action 1020 that relates to handling of a product can use an icon similar to a test tube image, but which may also graphically represent a cap 1022 covering the test tube. Such product action may also identify a product to be handled such as DNA.

Actions 1030 that relate to the conducting tests can be indicated as a test "worksheet" and may identify the particular medical condition to be investigated, such as, for example, EBV (Epstein-Barr virus). Such test worksheet actions may be shown on a display with an icon that graphically represents a plurality of capped test tubes in a tube holder, for example. Still another type of action that can be displayed on the screen is one that relates to the review or analysis of a test. For example, FIG. 10 displays actions 1040 that relate to "Test EBV Test Review" and Test EBV Test Analyzed" that are displayed with icons that graphically represent the display of test results.

In one embodiment, the information displayed about each action in the flow diagram (FIGS. 9-10) can be controlled in accordance with certain rules, as indicated in Table 1 below.

TABLE 1

| | Order Entry |
|---|---|
| Tube Actions | For Tube Actions word 'Tube' and Tube # or Tube ID are displayed depending on Options Setup. When both options to display Tube # and Tube ID are turned on, only Tube # is displayed |
| Product Actions | For Product Actions, product code and Tube # or Tube ID are displayed depending on Options Setup. When both options to display Tube # and Tube ID are turned on, only Tube # is displayed |
| Test Actions | For Test Actions words 'Worksheet', 'Test', Worksheet # and Test Code are displayed. |
| Preliminary Report Actions | For Preliminary Report Actions word 'Preliminary Report' is displayed |
| Final Report Actions | For Final Report Actions word 'Final Report' is displayed |
| Supplemental Report Actions | For Supplemental Report Actions word 'Supplemental Report' is displayed |
| Test Specific Report Actions | For Test Specific Report Actions word 'Test' and Test Code are displayed |

Figure 11:
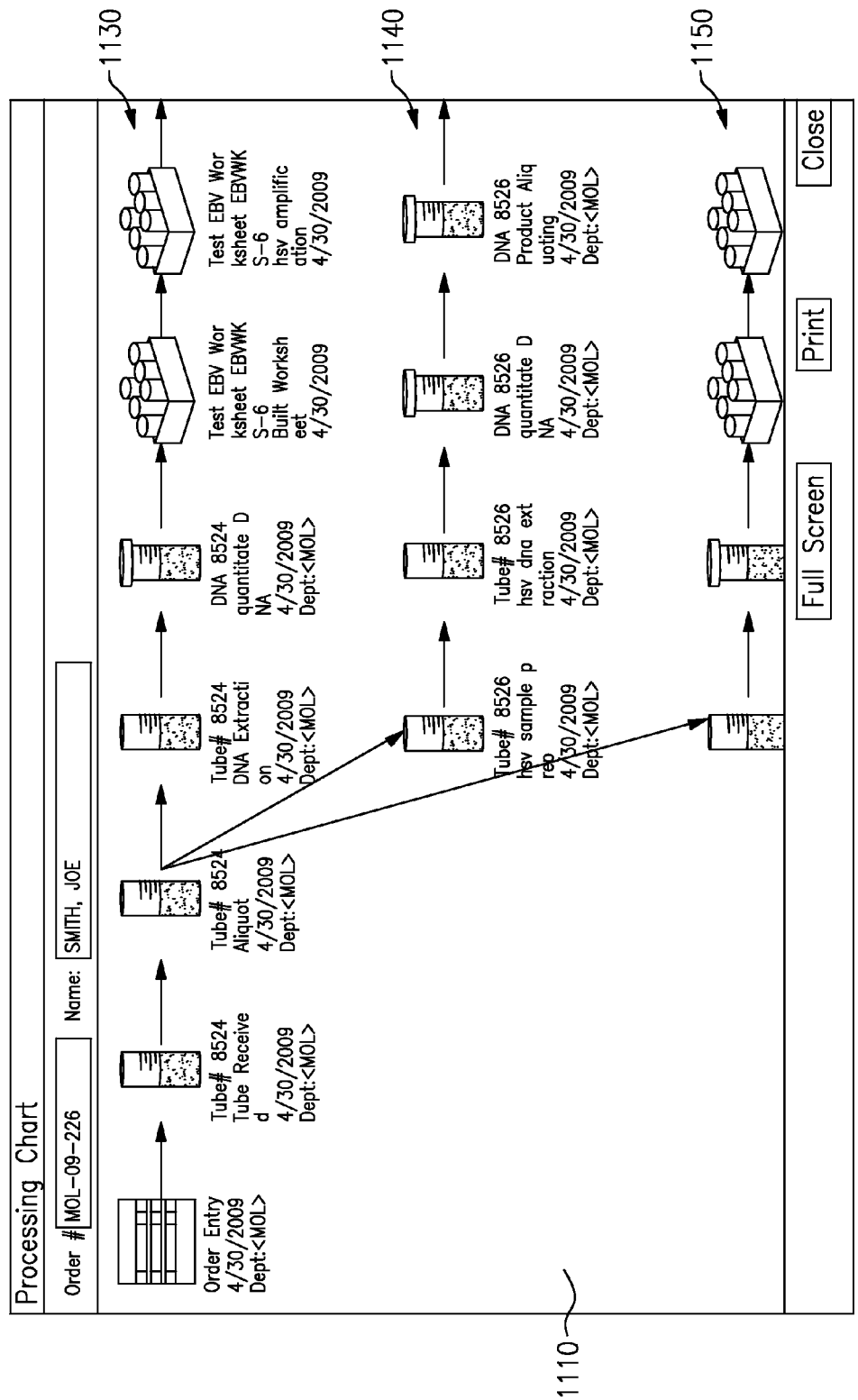
FIG. 11 illustrates a screen showing result of user manipulation of a flow diagram which can be displayed in accordance with an embodiment of the invention.

FIG. 11 illustrates a feature in accordance with one embodiment of the invention. FIG. 11 displays actions on the screen 1110 in a way similar to that of FIG. 8 in that it displays all the same icons as FIG. 8 but does not contain all the same text. The way actions are displayed in FIG. 11 is a result of manipulation by the user starting from a screen such as FIG. 8 which is displayed by the information processing system automatically when the user requests display of such screen. For example, the user can manipulate the display of icons on the screen, so as to move the icons representing one or a plurality of actions on the display from one location to another. For example, as illustrated in FIG. 11, the user can use a mouse having a displayed cursor 1115 to select the lower two rows of icons 1140, 1150 and drag such icons in a direction away from a higher row 1130 of icons. A result of dragging the icons to a lower location of the screen is that there is now more space between the higher row 1130 and middle row 1140 of icons. In addition, the icons may have been dragged so far lower that the text accompanying the lower row 1150 of icons no longer appears. However, the text for such lower row 1150 may still become visible when the user scrolls the screen downward to view the text.

Moreover, as further seen in FIG. 11, the arrows between an action and other actions which follow such action are intact after user manipulation. Despite the user manipulation, the arrows still show the relationships between actions and the order in which the actions should be performed. Other manipulation of the screen FIG. 11 that can be performed by the user may include reshaping one or more rows 1130, 1140 or 1150 of icons to display such row having a curved path along the screen between icons.

While the invention has been described in accordance with certain preferred embodiments thereof, those skilled in the art will understand the many modifications and enhancements which can be made thereto without departing from the true scope and spirit of the invention, which is limited only by the claims appended below.

What is claimed is:

1. An information processing system, comprising:
a processor; and
instructions executable by the processor to perform a method, the method including:
a) receiving user input in response to prompts on a display, the user input identifying a processable medical item being at least one of a medical sample or medical product, the medical sample being at least one of a specimen obtained by collection from a human, animal, plant or other living thing or formerly living thing, the medical product being an item preparable from a medical sample being at least one of a specimen obtained by collection from a human, animal, plant or other living thing or formerly living thing, and the user input selecting each of a plurality of discrete actions for handling the medical item, the actions having an at least implied order to be performed,
wherein the prompts on the display include at least one prompt for user input to select a type of specimen to be collected and at least one prompt for user input to select a test to be performed;
b) based on the received user input, storing identification information identifying the medical item and storing action information representing the selected actions; and
c) displaying at least some of the action information in form of a flow diagram representing the medical item with at least some of the identification information identifying the represented medical item, the flow diagram depicting at least some of the selected actions automatically arranged in the at least implied order,
wherein the action information displayable in the form of the flow diagram represents two or more actions to be performed in parallel on two or more items divided from one item due to an aliquot action, and the positions of the represented actions in the flow diagram graphically represents a parallel order in which the two or more actions are to be performed in parallel, and graphically represents a sequential order in which at least some of the actions are to be performed in sequence, and wherein the action information displayable in the form of the flow diagram identifies each of the two or more items divided from the one item due to the aliquot action.

2. An information processing system as claimed in claim 1, wherein the actions are selected from a predefined protocol, the predefined protocol defining the order in which the actions are to be performed.

3. An information processing system as claimed in claim 1, wherein the medical item includes a medical sample and at least one of the selected actions includes processing to prepare a medical product from the medical sample.

4. An information processing system as claimed in claim 1, wherein the method further comprises a step of (d) displaying a table containing at least some of the action information and at least some of the identification information.

5. An information processing system as claimed in claim 4, wherein step (d) includes displaying the table with the selected actions automatically arranged in the at least implied order.

6. An information processing system as claimed in claim 1, wherein the actions are selected from a plurality of different types, and wherein step (c) is performed so that the flow diagram depicts the at least some selected actions on the flow diagram with a plurality of icons and depicts the medical item with an icon, each icon corresponding to at least one of: an action from among the different types of the actions, or a medical item from among a plurality of different types of medical items.

7. An information processing system as claimed in claim 6, wherein each of the icons graphically represents at least one of: the corresponding type of the action or the corresponding type of medical item.

8. An information processing system as claimed in claim 1, wherein the method further comprises manipulating the display of the at least some selected actions depicted on the flow diagram in response to user input to the displayed flow diagram.

9. A non-transitory computer-readable recording medium having a plurality of instructions recorded thereon, the instructions being executable by a processor to perform a method, the method comprising:
   a) receiving user input in response to prompts on a display, the user input identifying a processable medical item being at least one of a medical sample or medical product, the medical sample being at least one of a specimen obtained by collection from a human, animal, plant or other living thing or formerly living thing, the medical product being an item preparable from a medical sample being at least one of a specimen obtained by collection from a human, animal, plant or other living thing or formerly living thing, and the user input selecting each of a plurality of discrete actions for handling the medical item, the actions having an at least implied order to be performed,
   wherein the prompts on the display include at least one prompt for user input to select a type of specimen to be collected and at least one prompt for user input to select a test to be performed;
   b) based on the received user input, storing identification information identifying the medical item and storing action information representing the selected actions; and
   c) displaying at least some of the action information in form of a flow diagram representing the medical item with at least some of the identification information identifying the represented medical item, the flow diagram depicting at least some of the selected actions automatically arranged in the at least implied order,
   wherein the action information displayable in the form of the flow diagram represents two or more actions to be performed in parallel on two or more items divided from one item due to an aliquot action, and the positions of the represented actions in the flow diagram graphically represents a parallel order in which the two or more actions are to be performed in parallel, and graphically represents a sequential order in which at least some of the actions are to be performed in sequence, and wherein the action information displayable in the form of the flow diagram identifies each of the two or more items divided from the one item due to the aliquot action.

10. The non-transitory computer-readable recording medium as claimed in claim 9, wherein the actions are selected from a predefined protocol, the predefined protocol defining the order in which the actions are to be performed.

11. The non-transitory computer-readable recording medium as claimed in claim 9, wherein the method further comprises a step of (d) displaying a table containing at least some of the action information and at least some of the identification information.

12. The non-transitory computer-readable recording medium as claimed in claim 11, wherein step (d) includes displaying the table with the selected actions automatically arranged in the at least implied order.

13. The non-transitory computer-readable recording medium as claimed in claim 9, wherein the actions are selected from a plurality of different types, and wherein step (c) is performed so that the flow diagram depicts the at least some selected actions on the flow diagram with a plurality of icons and depicts the medical item with an icon, each icon corresponding to at least one of: an action from among the different types of the actions, or a medical item from among a plurality of different types of medical items.

14. The non-transitory computer-readable recording medium as claimed in claim 9, wherein the method further comprises manipulating the display of the at least some selected actions depicted on the flow diagram in response to user input to the displayed flow diagram.

15. A method of operating a medical information processing system containing a processor, comprising:
   a) receiving user input in response to prompts on a display, the user input identifying a processable medical item being at least one of a medical sample or medical product, the medical sample being at least one of a specimen obtained by collection from a human, animal, plant or other living thing or formerly living thing, the medical product being an item preparable from a medical sample being at least one of a specimen obtained by collection from a human, animal, plant or other living thing or formerly living thing, and the user input selecting each of a plurality of discrete actions for handling the medical item, the actions having an at least implied order to be performed,
   wherein the prompts on the display include at least one prompt for user input to select a type of specimen to be collected and at least one prompt for user input to select a test to be performed;
   b) based on the received user input, storing identification information identifying the medical item and storing action information representing the selected actions; and
   c) displaying at least some of the action information in form of a flow diagram representing the medical item with at least some of the identification information identifying the represented medical item, the flow diagram depicting at least some of the selected actions automatically arranged in the at least implied order,
   wherein the action information displayable in the form of the flow diagram represents two or more actions to be performed in parallel on two or more items divided from one item due to an aliquot action, and the positions of the represented actions in the flow diagram graphically represents a parallel order in which the two or more actions are to be performed in parallel,
   and wherein the action information displayable in the form of the flow diagram identifies each of the two or more items divided from the one item due to the aliquot action, wherein one of the two or more items retains the same identifying information as the one item prior to being divided into the two or more items.

16. A method as claimed in claim 15, wherein the method further comprises a step of (d) displaying a table containing at least some of the action information and at least some of the identification information.

17. A method as claimed in claim 16, wherein step (d) includes displaying the table with the selected actions automatically arranged in the at least implied order.

18. A method as claimed in claim 15, wherein the actions are selected from a plurality of different types, and wherein step (c) is performed so that the flow diagram depicts the at least some selected actions on the flow diagram with a plurality of icons and depicts the medical item with an icon, each icon corresponding to at least one of: an action from among the different types of the actions, or a medical item from among a plurality of different types of medical items.

19. A method as claimed in claim 18, wherein each of the icons graphically represents at least one of: the corresponding type of the action or the corresponding type of medical item.

20. A method as claimed in claim 15, wherein the method further comprises manipulating the display of the at least some selected actions depicted on the flow diagram in response to user input to the displayed flow diagram.

* * * * *